United States Patent [19]

Chang et al.

[11] Patent Number: 4,540,497

[45] Date of Patent: Sep. 10, 1985

[54] FLUOROALIPHATIC RADICAL-CONTAINING, SUBSTITUTED GUANIDINES AND FIBROUS SUBSTRATES TREATED THEREWITH

[75] Inventors: John C. Chang; Richard D. Howells, both of St. Paul, Minn.

[73] Assignee: Minnesota Mining and Manufacturing Company, St. Paul, Minn.

[21] Appl. No.: 440,330

[22] Filed: Nov. 9, 1982

[51] Int. Cl.³ ............................................. D06M 15/00
[52] U.S. Cl. ....................................... 252/8.8; 560/24; 564/230; 564/236
[58] Field of Search ........................... 252/8.8; 560/24; 564/230, 236; 544/159, 85

[56] References Cited

U.S. PATENT DOCUMENTS

| | | | |
|---|---|---|---|
| 2,853,473 | 9/1958 | Campbell et al. | 260/77.5 |
| 2,941,966 | 6/1960 | Campbell | 260/2.5 |
| 3,329,661 | 7/1967 | Smith et al. | 260/79.3 |
| 3,458,571 | 7/1969 | Tokoli | 260/556 |
| 3,574,791 | 4/1971 | Sherman et al. | 260/884 |
| 3,728,151 | 4/1973 | Sherman et al. | 117/138.8 A |
| 3,862,989 | 1/1975 | Hansen | 260/606.5 P |
| 3,896,251 | 7/1975 | Landucci | 428/290 |
| 3,916,053 | 10/1975 | Sherman et al. | 428/96 |
| 4,013,627 | 3/1977 | Temple | 526/245 |
| 4,024,178 | 5/1977 | Landucci | 260/472 |
| 4,067,820 | 1/1978 | Wagner et al. | 252/426 |
| 4,144,367 | 3/1979 | Landucci | 428/96 |
| 4,165,338 | 8/1979 | Katsushima et al. | 260/584 R |
| 4,174,433 | 11/1979 | Schafer et al. | 528/49 |
| 4,215,205 | 7/1980 | Landucci | 525/331 |
| 4,264,484 | 4/1981 | Patel | 260/29.6 F |
| 4,325,857 | 4/1982 | Champaneria et al. | 523/412 |

OTHER PUBLICATIONS

Banks, R. E. Ed., "Organofluorine Chemicals and Tehir Industrial Applications", Ellis Horwood, Ltd., West Sussex, England, 226-230, (1979).

Kruzer et al., Chemical Reviews, 67, 107, (1967).

K. Wagner et al., Angewante Chemie Int. Ed., 20, 819, (1981).

Kirk-Othmer, Encyclopedia of Polymer Science Technology, 8, 374-404, (1968).

Primary Examiner—Paul Lieberman
Assistant Examiner—Willie Thompson
Attorney, Agent, or Firm—Donald M. Sell; James A. Smith; Carole Truesdale

[57] ABSTRACT

Novel fluoroaliphatic radical-containing, substituted guanidines useful in the form of organic solutions or aqueous dispersions in the treatment of fibrous substrates, such as textile fibers, to impart oil and water repellency.

17 Claims, No Drawings

FLUOROALIPHATIC RADICAL-CONTAINING, SUBSTITUTED GUANIDINES AND FIBROUS SUBSTRATES TREATED THEREWITH

This invention relates to the treatment of fibrous substrates, such as textile fibers, paper, and leather, with fluorochemical compositions to impart oil and water repellency, and to the resulting treated substrates. In another aspect, it relates to the treatment of carpet fiber with a finish comprising a fluoroaliphatic radical-containing composition to impart oil and water repellency and soil resistance to such fiber. In another aspect, it relates to fluoroaliphatic radical-containing compositions, and their preparation, which are useful in such treatment.

In the industrial production of textiles, such as carpet and apparel, and such other fibrous substrates as paper and leather, it is common to treat such substrates with fluorochemicals containing fluoroaliphatic radicals (often designated by the symbol "$R_f$") to impart oil and water repellency to the surface of such substrates. Fluorochemicals of this type and their application to fibrous substrates are described in various prior art publications, e.g., U.S. Pat. Nos. 3,329,661 (Smith et al), 3,458,571 (Tokoli), 3,574,791 (Sherman et al), 3,728,151 (Sherman et al), 3,916,053 (Sherman et al), 4,144,367 (Landucci), 3,896,251 (Landucci), 4,024,178 (Landucci), 4,165,338 (Katsushima et al), 4,215,205 (Landucci), 4,013,627 (Temple), 4,264,484 (Patel), 4,325,857 (Champaneria et al), and Banks, R. E., Ed. "Organofluorine Chemicals and their Industrial Applications", Ellis Horwood, Ltd., West Sussex, England, 226-230 (1979).

Although some fluorochemicals are useful in many applications and many are commercial products, some are relatively expensive to prepare and apply, others are difficult to apply, and others are not durable or do not impart the required properties to the extent desired.

Conventionally, fluorochemical compositions have been commercially applied as a top coating to the finished fibrous article, such as carpet. Recently, several fluorochemical compositions have been commercially applied to textile fiber or yarn during its manufacture before it is woven or fabricated into the finished article. However, some of these fluorochemical compositions have had limited success for various reasons including incompatibility or reactivity of the fluorochemical with fiber finish components such as lubricants, lack of durability of the fluorochemical on the treated fiber to dyeing or other fiber manufacturing operations, and insufficient water and oil repellency and soil resistance in the finished article.

It is an object of this invention to provide fluoroaliphatic radical-containing, substituted guanidines (hereinafter often called fluorochemical guanidines for brevity) useful for treating textile fibers and other fibrous substrates to impart oil and water repellency thereto.

Another object of this invention is to provide fluorochemical guanidines which can be used to treat textile fibers in combination with or as a component of fiber finishes, e.g. spin-finish lubricants, such guanidines being compatible with said fiber finishes and not interfering with normal textile fiber processing steps.

A further object of this invention is to provide fluorochemical-treated textile fiber with a high percentage of the fluorochemical retained on the fiber through fiber processing and dyeing steps, and with durable water and oil repellency and soil resistance properties.

It is yet another object of this invention to provide fluorochemical guanidines which can be used in the form of organic solutions or aqueous dispersions to treat fibrous substrates such as textile fibers, filaments, yarns, or finished fibrous articles, e.g. carpets, and other fibrous substrates such as paper and leather, to impart oil and water repellency thereto.

Briefly, this invention provides, in one aspect, normally solid, water-insoluble, fluorochemical guanidine compositions which are fluoroaliphatic radical-containing, substituted (wholly or partially) guanidine compounds, or compositions comprising or consisting essentially of mixtures of said compounds, which compounds have one or more monovalent fluoroaliphatic radicals ($R_f$) and one or more substituted guanidino moieties, such radicals and moieties bonded together by hetero atom-containing or organic linking groups preferably comprising carbamato (urethane) groups, such fluorochemical guanidines being useful in the form of organic solutions or aqueous dispersions in the treatment of fibrous substrates, such as textile fibers (or filaments) during their manufacture, and useful also in the treatment of finished or fabricated fibrous substrates such as carpets, paper, and leather, to impart oil and water repellency to the surface thereof.

A class of such fluorochemical guanidines can be represented by the general formula

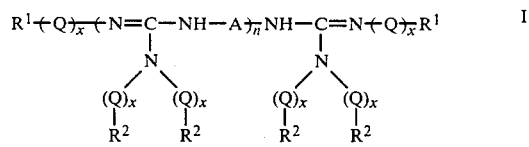

which formula generically encompasses individual compounds or represents a mixture of such compounds as they are obtained from reactions used in their preparation.

Guanidines are conveniently prepared by the reaction of carbodiimides and imino (>NH) compounds, e.g. amines, hydrazines, hydrazides, and amides, using general routes for guanidine synthesis as described, for example, by Kurzer, et al, *Chemical Reviews*, 67, 107, (1967), and in U.S Pat. No. 4,174,433 (Schafer, et al). In addition, carbodiimides can be prepared from ureas, thioureas, and other compounds as described by K. Wagner et al., *Angewante Chemie Int. Ed.*, 20, 819 (1981). Many fluorochemical guanidines of this invention can be prepared in an analogous manner from fluorochemical carbodiimides and said imino compounds. Such fluorochemical carbodiimide and their preparation are described in U.S. Pat. No. 4,024,178 (Landucci), which description is incorporated herein by reference thereto.

In formula I, "n" is a number (in the case where the formula is that of a mixture) or an integer (in the case where the formula is that of a compound) of 0 up to 20, preferably 0 to 10 and most preferably 0 to 5, and "x" is 0 or 1. Each Q is the same or different divalent linking group. A is a divalent organic linking group which can contain a fluoroaliphatic radical, $R_f$, each A being the same or different. Each $R^1$ is the same or different and is selected from H, $R_f$, and terminal monovalent organic radicals such as alkyl, cycloalkyl, aryl, and combinations thereof, e.g. aralkyl, which radicals can contain hetero moieties, e.g. —O—, —S—,

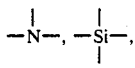

and —CO—, and is preferably free of active (or isocyanate-reactive) hydrogen atoms (i.e., hydrogen atoms of groups, such as mercapto, amino, carboxyl, and aliphatic hydroxyl groups, that can react readily with isocyanate under urethane bond-forming conditions, e.g., 20° to 100° C.). Generally, $R^1$ will have no more than about 18 carbon atoms. Where $R^1$ is said $R_f$, the subscript x of the adjacent Q must be 1 and not 0 because $R_f$ cannot be directly bonded to a N-atom of the guanidino group. Unless otherwise indicated, "R" means either $R^1$ or $R^2$. Each $R^2$ is like $R^1$ but in addition the two $R^2$ groups of a guanidino group can be bonded together to form a cyclic structure with the adjacent N atom of that guanidino group. There is at least one $R_f$ radical present in one or more of the $R^1$, $R^2$, and A groups for a given compound. When only one guanidino moiety is present, and only two organic substituents are in said guanidino moiety, said substituents must be on different N atoms of the moiety.

In the above general formula I, the divalent organic linking group A connects successive guanidino moieties when n is 1 or more. Illustrative linking groups A are alkylene groups, such as ethylene, isobutylene, hexylene, and methylenedicyclohexylene, having 2 to about 20 carbon atoms, aralkylene groups, such as —CH$_2$C$_6$H$_4$CH$_2$— and —C$_6$H$_4$CH$_2$C$_6$H$_4$—, having up to 20 carbon atoms, arylene groups, such as tolylene, —C$_6$H$_3$(CH$_3$)—, polyoxaalkylene groups, such as —(C$_2$H$_4$O)$_y$C$_2$H$_4$— where y is 1 to about 5, and various combinations of these groups. Such groups can also include other hetero moieties (besides —O—), including —S— and

However, A is preferably free of groups with said active hydrogen atoms.

The A group can be a residue of an organic diisocyanate (from which the carbodiimido and guanidino moieties can be derived by successive reactions), that is, A can be the divalent radical obtained by removal of the isocyanate groups from an organic diisocyanate. Suitable diisocyanate precursors may be simple, e.g. tolylene-2,4-diisocyanate, methylene bis(4-phenyleneisocyanate), and mixtures thereof, or complex, as formed by the reaction of a simple diisocyanate with an organic diol or polyol in appropriate proportions to yield an isocyanate-terminated polyurethane. Other isocyanates can also be used as starting materials. Some of these are described, for example, in U.S. Pat. No. 4,174,433. Representative A groups include —CH$_2$C$_6$H$_4$CH$_2$C$_6$H$_4$CH$_2$—, —C$_6$H$_3$(CH$_3$)—, —C$_6$H$_{10}$CH$_2$C$_6$H$_{10}$—, —(CH$_2$)$_6$—, —C$_6$H$_4$CH$_2$C$_6$H$_4$—, and C$_8$F$_{17}$SO$_2$N[C$_2$H$_4$OCONHC$_6$H$_3$(CH$_3$)—]$_2$. Although the fluorochemical guanidines of this invention generally and preferably are derived from diisocyanates, the fluorochemical guanidines can be derived from triisocyanates, e.g. OCNC$_6$H$_4$CH$_2$C$_6$H$_3$(NCO)CH$_2$C$_6$H$_4$NCO. A mixture of di- and tri-isocyanates can be used to provide fluorochemical guanidines which are branched but still retain the desired solubility and dispersibility characteristics of the linear fluorochemical guanidines depicted by formula I.

The R-Q groups are preferably radicals derived from isocyanate compounds and can be aliphatic, e.g. C$_6$H$_{13}$—, aromatic, e.g. C$_6$H$_5$—, aralkyl, e.g. C$_6$H$_5$CH$_2$—, fluoroaliphatic, e.g. C$_6$F$_{13}$CH$_2$—, C$_7$F$_{15}$CH$_2$OCONHC$_6$H$_3$(CH$_3$)—, and C$_8$F$_{17}$SO$_2$N(CH$_3$)C$_2$H$_4$OCONHC$_6$H$_4$CH$_2$C$_6$H$_4$—. The organic R—Q radicals can have a variety of other structures, and can contain hetero atom-containing moieties, e.g. —O—, —S—, and

but, as with the A group, it is preferably free of groups containing said active hydrogen atoms.

The fluoroaliphatic radical, $R_f$, is a fluorinated, stable, inert, non-polar, preferably saturated, monovalent moiety which is both oleophobic and hydrophobic. It can be straight chain, branched chain, and, if sufficiently large, cyclic, or combinations thereof, such as alkylcycloaliphatic radicals. The skeletal chain can include catenary oxygen, hexavalent sulfur, and/or trivalent nitrogen hetero atoms bonded only to carbon atoms, such hetero atoms providing stable linkages between fluorocarbon portions of $R_f$ and not interferring with the inert character of the $R_f$ radical. While $R_f$ can have a large number of carbon atoms, compounds where $R_f$ is not more than 20 carbon atoms will be adequate and preferred since large radicals usually represent a less efficient utilization of fluorine than is possible with smaller $R_f$ radicals. The large radicals also are generally less soluble in organic solvents. Generally, $R_f$ will have 3 to 20 carbon atoms, preferably 6 to about 12, and will contain 40 to 78 weight percent, preferably 50 to 78 weight percent, fluorine. The terminal portion of the $R_f$ group has at least three fully fluorinated carbon atoms, e.g. CF$_3$CF$_2$CF$_2$—, and the preferred compounds are those in which the $R_f$ group is fully or substantially completely fluorinated, as in the case where $R_f$ is perfluoroalkyl, $C_nF_{2n+1}$.

Generally, the fluorochemical guanidine will contain about 20 to 70 weight percent, preferably about 25 to 50 weight percent, of carbon-bonded fluorine. If the fluorine content is less than about 20 weight percent, impractically large amounts of the fluorochemical guanidine will generally be required, while fluorine contents greater than about 70 weight percent are unnecessary to achieve the desired surface properties and thus represent an uneconomical use of fluorine and may also present compatibility problems where it is desired to apply the fluorochemical guanidine as an organic solution thereof.

The function of the linking group Q in formula I is to bond the R groups to the N atoms of the guanidino units. Q can comprise a hetero atom-containing group or an organic group or a combination of such groups, examples of which are polyvalent aliphatic, e.g., —CH$_2$—, —CH$_2$CH$_2$—, and —CH$_2$CH(CH$_2$—)$_2$, polyvalent aromatic, oxy, thio, carbonyl, sulfone, sulfoxy, —N(CH$_3$)—, sulfonamido, carbonamido, sulfonamidoalkylene, carbonamidoalkylene, carbonyloxy, urethane, e.g., —CH$_2$CH$_2$OCONH—, and urea, e.g., —NHCONH—. The linkage Q for a specific fluorochemical guanidine useful in this invention will be dictated by the ease of preparation of such a compound and the availability of necessary precursors thereof. From the above description of Q, it is apparent that this linkage can have a wide variety of structures. However, as with the R and A groups, Q is preferably free of moieties having said active hydrogen atoms. However large Q is, the fluorine content (the locus of which is $R_f$) of the fluorochemical guanidine is in the aforementioned limits.

It should be recognized that, in the above general formula I, isomeric or tautomeric forms may be present. For example, for a given guanidino unit, the following tautomeric forms can exist:

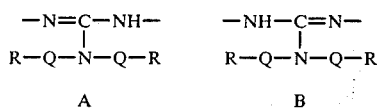

When R—Q is H, then another isomeric structure can also be present:

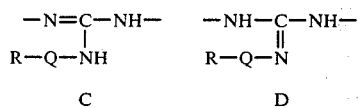

All of the above tautomeric and isomeric forms, as well as mixed $R_f$ groups and other organic moieties, can be present and are included in the fluorochemical guanidines of this invention.

The fluorochemical guanidines of this invention are normally solid (i.e., solid at 20° C.) with melting points preferably in the range of 40° to 150° C. They are preferably soluble to the extent of at least 10 weight percent in ethyl acetate at 20° C.

The above-described fluorochemical guanidines can be prepared by successive substitutions on guanidine, or by conversion of precursor carbodiimides to guanidines via reaction with imino compounds (i.e., compounds containing >NH), such as primary or secondary amines. The imino compounds may contain a fluoroaliphatic radical in the instance where the carbodiimide precursor contains a fluoroaliphatic radical, and must contain a fluoroaliphatic radical in the instance where the carbodiimide precursor does not contain a fluoroaliphatic radical.

Fluoroaliphatic radical-containing intermediates ($R_f$ intermediates) generally are commercially made by electrochemical fluorination of organic acids or halides thereof, or by telomerization of tetrafluoroethylene, followed by known reactions to form intermediates that contain a hydroxyl group that is capable of reaction with an isocyanate group to form a urethane linkage (—OCONH—). Such urethane-forming reactions are generally carried out neat or in the presence of non-reactive solvents, such as ethyl acetate or methyl ethyl ketone, at moderate temperatures, such as 20° to 130° C. Catalysts for the urethane formation may be employed, but are unnecessary, and in some cases undesirable when aromatic diisocyanates are employed.

The mixture of urethane group-containing isocyanates and non-urethane-containing isocyanates are then converted to the carbodiimide precursors of the fluorochemical guanidines of this invention after addition of low levels (e.g., 0.05 to 1.5 weight percent of reactants) of a catalyst. There are many catalysts known to effect carbodiimide formation from isocyanates. Two of the most effective classes are phospholene oxides (described in U.S. Pat. Nos. 2,853,473, 2,941,966, and 4,067,820) and phosphine oxides (described in U.S. Pat. No. 3,862,989). The carbodiimide is then added neat or as an organic solvent solution to the imino compound. This mode of addition as well as moderate temperatures are generally employed to minimize the addition of a guanidino N—H moiety to a carbodiimide which generally leads to reaction mixtures that have considerably lower organic solvent solubility.

Representative reaction schemes for the preparation of fluorochemical guanidines of this invention are outlined below, where the product designated as I' are species of formula I supra.

Scheme 1

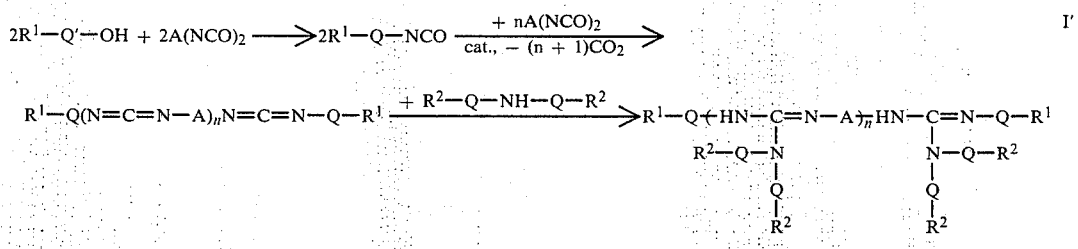

Scheme 2

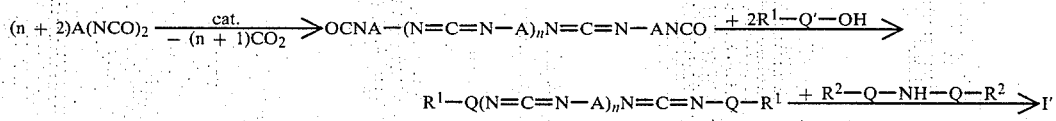

Scheme 3

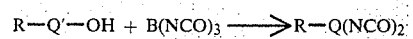

R—Q(NCO)$_2$ + B(NCO)$_3$ + A(NCO)$_2$ + R$^1$—QNCO $\xrightarrow[-CO_2]{cat.}$ Mixed carbodiimide The mixtures of fluorochemical guanidines of this invention may contain small amounts of fluorochemical diurethane compounds (e.g., R—Q'—OCONH—A—NHCOO—Q'—R, a possible by-product in Scheme 1) free of guanidino groups due to the synthetic procedures generally followed. The amount of this by-product depends on the mode of addition, molar ratio of reactants, and the relative reactivity of isocyanate functional groups. The mixture of fluorochemical guanidines may contain small or minor amounts of compounds that arise from reaction of an initially formed guanidine with a carbodiimide group to give a higher molecular weight fluorochemical guanidine.

Fluorochemical guanidines in which some of the precursor carbodiimide moieties (in cases where n is greater than 1) have not been reacted with an imino compound are also included as fluorochemical guanidines of this invention.

Representative $R_f$ intermediates for the preparation of fluorochemical guanidines of this invention include:

$C_8F_{17}SO_2N(C_2H_5)C_2H_4OH$
$C_8F_{17}C_2H_4OH$
$C_7F_{15}CH_2OH$
$C_7F_{15}CON(C_2H_5)C_2H_4OH$
$C_8F_{17}C_2H_4SC_2H_4OH$
$(CF_3)_2CF(CF_2)_8C_2H_4OH$
$(CF_3)_2CFOC_2F_4C_2H_4OH$
$C_8F_{17}C_2H_4SO_2N(CH_3)C_4H_8OH$
$C_8F_{17}SO_2N(CH_3)C_3H_6NH_2$

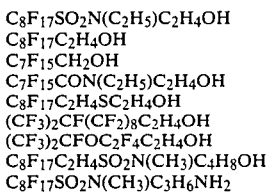

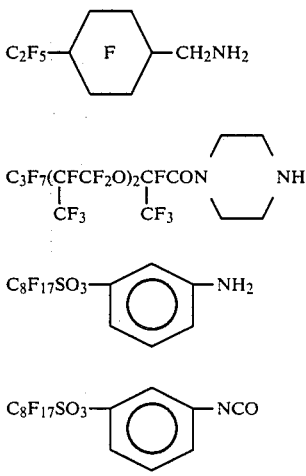

$C_8F_{17}C_6H_4NH_2$
$C_8F_{17}C_6H_4NCO$
$C_7F_{15}CH_2NCO$

Representative organic isocyanates include:
tolylene-2,4-diisocyanate
hexamethylene diisocyanate
methylenebis(4-phenyleneisocyanate)
methylenebis(4-cyclohexyleneisocyanate)
xylylene diisocyanate
1-methoxy-2,4-phenylene diisocyanate
1-chlorophenyl-2,4-diisocyanate,
p-(1-isocyanatoethyl)phenyl isocyanate
phenyl isocyanate
m-tolyl isocyanate
2,5-dichlorophenyl isocyanate
hexyl isocyanate Representative imino compounds include the following: ammonia, methylamine, ethylamine, butylamine, diethylamine, diisopropylamine, dibutylamine, ethyleneimine, morpholine, piperidine, N,N-dimethyl hydrazine, aniline, 3-aminopropyltrimethoxysilane, pyrrolidine, pyrrolidone, imidazole, guanidine, acetamidine, 2-methoxyethylamine, hexamethylenediamine, piperazine, formamide, acetyl hydrazide, sebacoyl dihydrazide.

In cases where certain imino compounds, e.g. ethylene imine, guanidine, N,N'-dialkyl hydrazine, ethylene diamine, and hydrazides, are reacted with fluorochemical carbodiimide precursors (Scheme 1, where the above imino compounds are used), adducts are formed which can rearrange to cyclic guanidino structures. These cyclic forms are also included as fluorochemical guanidine compounds of this invention.

Substrates which can be treated in accordance with this invention are textile fibers (or filaments), and finished or fabricated fibrous articles such as textiles, e.g. carpet, paper, paperboard, leather, and the like. The textiles include those made from natural fibers, such as cotton and wool, and those made from synthetic organic fibers, such as nylon, acetate, rayon, acrylic, and polyester fibers. Especially good results are obtained on nylon and polyester fibers. The fibers or filaments as such or in an aggregated form, e.g. yarn, tow, web, or roving, or the fabricated textile, e.g., articles such as carpet and woven fabrics, can be treated with the fluorochemical guanidines. The treatment can be carried out by applying the fluorochemical guanidines as organic solutions or aqueous or organic dispersions by known techniques customarily used in applying fluorochemicals, e.g. fluorochemical acrylate copolymers, to fibers and fibrous substrates. (If desired, such known fluorochemicals can be used in conjunction with the fluorochemical guanidines, as will be shown below.) For example, the fluorochemical treatment can be by immersing the fibrous substrates in a bath containing the fluorochemical guanidine, padding the substrate or spraying the same with the fluorochemical guanidine, or by foam, kiss-roll, or metering applications, e.g. spin finishing, and then drying the treated substrates if solvent is present. If desired, the fluorochemical guanidine can be co-applied with conventional fiber treating agents (or adjuvants), e.g. antistatic agents or neat oils (fiber lubricants).

In the manufacture of synthetic organic fibers (see, for example, review articles in Kirk-Othmer, *Encyclopedia of Polymer Science and Technology*, 8, 374–404, 1968), the first step that normally takes place in the process, following initial formation of the filaments (e.g. by melt spinning or solvent spinning), is coating the fiber surface with a small amount (generally less than 2% active solids on fiber) of fiber finish comprising lubricating and antistatic agents. It is particularly advantageous to treat such textile fibers, e.g. nylon 6, with the fluorochemical guanidines of this invention in conjunction with the spin finish being applied to such textile fibers.

Fiber finishes are generally produced in the form of dilute aqueous emulsions or as an oil ("neat oil") which principally contains said lubricant and antistatic agent as well as emulsifier (surfactant) and may also contain materials such as antioxidants.

Representative lubricants include mineral oils, waxes, vegetable oils (triglycerides) such as coconut oil, peanut oil, and castor oil, synthetic oils, such as esters, polyoxyethylene derivatives of alcohols and acids, and silicone oils.

The antistatic agents, emulsifiers, and surfactants incorporated into the fiber finish are selected from similar chemical classes, which include:

(a) anionics, such as fatty acid soaps, sulfated vegetable oils, salts of alkyl and ethoxylated alkyl phosphates;
(b) cationics, such as fatty amines, quaternary ammonium compounds, and quaternary phosphonium compounds;
(c) nonionics, such as glyceryl monooleate, ethoxylated alcohols, ethoxylated fatty acid, and ethoxylated fatty amides; and
(d) amphoterics, such as betaines, amino acids and their salts.

The preferred mode of applying the fluorochemical guanidines of this invention to synthetic organic fibers is to incorporate them into the above-described fiber finishes in an amount sufficient to achieve the desired properties, oil and water repellency and soil resistance. Generally, the amount of fluorochemical guanidine to be used will be that sufficient to retain on the fiber of the finished article, e.g., carpet, about 200 to 1600 ppm fluorine based on the weight of the fiber. Such additions to the conventional fiber finish can be carried out without sacrificing or adversely affecting typical requirements that conventional fiber finishes must meet, namely lubrication, thermal stability, low fuming at elevated temperature, and wetting for fiber dyeability (color addition). The conventional finish components of the fiber finishes containing the fluorochemical guanidines of this invention are removed in a conventional manner after the fiber is manufactured in fabric form, e.g., carpets and upholstery fabrics. The fluorochemical guanidines withstand the typical conditions encountered during fiber and yarn processing and also survive the more severe processing conditions which the greige goods encounter, such as scouring and, dyeing, and the finished goods encounter, such as washing, steam cleaning, and dry cleaning. The fluorochemical guanidines do not interfere with, and are durable through, the normal fiber processing steps, e.g., drawing, texturizing, and heat setting, and provide oil and water repellency and anti-soiling properties to the finished article, e.g., carpet made from the treated fibers.

The conventional application methods used to apply finishes to fibers (or filaments) can be used with the fluorochemical guanidine finishes of this invention. Such methods include the use of either (a) a revolving ceramic cylinder, i.e., kiss-roll, which is partially immersed in a pan containing the finish, over which the moving filaments pass and pick up a thin film of finish, (b) a metering pump supplying finish through a slot or hole in a fiber guide over which the moving filaments pass, (c) an immersion finish bath, or (d) spraying devices.

The fluorochemical guanidines of this invention are generally compatible with (i.e., dispersible or sufficiently soluble in) commercial neat oil fiber finishes and thus may be mixed with them and coapplied (or applied before or after them). Solubilizing aids, such as "Carbitol" or "Cellosolve" solvents, can be added to the finish to enhance solubility of the fluorochemical guanidines in the neat oil finish.

Representative fluorochemical guanidines of this invention having the general formula II are shown in Table 1.

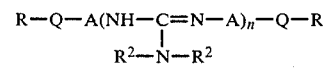

TABLE 1

| Compound No.* | R—Q | A | NR²R² |
|---|---|---|---|
| 1 | $C_8F_{17}$—$SO_2N(C_2H_5)C_2H_4OCONH$ | $C_6H_4CH_2C_6H_4$ | $N(C_4H_9)_2$ |
| 2 | $C_8F_{17}$—$SO_2N(C_2H_5)C_2H_4OCONH$ | $C_6H_4CH_2C_6H_4$ | $N(iC_3H_6)_2$ |
| 3 | $C_8F_{17}$—$SO_2N(C_2H_5)C_2H_4OCONH$ | $C_6H_4CH_2C_6H_4$ | $N(C_2H_5)_2$ |
| 4 | $C_8F_{17}$—$SO_2N(C_2H_5)C_2H_4OCONH$ | $C_6H_3(CH_3)$ | $NHCH(CH_3)_2$ |
| 5 | $C_8F_{17}$—$SO_2N(C_2H_5)C_2H_4OCONH$ | $C_6H_3(CH_3)$ | $NHC_{12}H_{25}$ |
| 6 | $C_8F_{17}$—$SO_2N(C_2H_5)C_2H_4OCONH$ | $C_6H_4CH_2C_6H_4$ | morpholino (N–O ring) |
| 7 | $C_8F_{17}$—$SO_2N(C_2H_5)C_2H_4OCONH$ | $C_6H_4CH_2C_6H_4$ | $NHN(CH_3)_2$ |
| 8 | $C_8F_{17}$—$SO_2N(C_2H_5)C_2H_4OCONH$ | $C_6H_3(CH_3)$ | $NHC_3H_6Si(OMe)_3$ |
| 9 | $C_8F_{17}$—$SO_2N(C_2H_5)C_2H_4OCONH$ | $C_6H_4CH_2C_6H_4$ | piperazino-$NSO_2C_8F_{17}$ |
| 10 | $(CH_3)_2CHCH_2$—$OCONH$ | $C_6H_4CH_2C_6H_4$ | piperazino-$NSO_2C_8F_{17}$ |

TABLE 1-continued

| Compound No.* | R—Q | A | NR²R² |
|---|---|---|---|
| 11 | $C_8F_{17}$—$SO_2N(C_2H_5)C_2H_4OCONH$ | $C_6H_4CH_2C_6H_4$ | N-H—⟨⟩—$O_3SC_8F_{17}$ |
| 12 | $C_8F_{17}$—$SO_2N(C_4H_9)C_2H_4OCONH$ | $C_6H_4CH_2C_6H_4$ | $N(C_4H_9)_2$ |
| 13 | $C_8F_{17}$—$C_2H_4OCONH$ | $C_6H_4CH_2C_6H_4$ | $N(C_4H_9)_2$ |
| 14 | $C_8F_{17}$—$C_2H_4OCONH$ | $C_6H_3(CH_3)$ | $N(C_4H_9)_2$ |

*For all compounds listed, n has an average value of 2, except for compound no. 4, where n has a value of about 1.8.

Objects and advantages of this invention are illustrated in the following examples.

EXAMPLE 1

In a 2-liter, 3-neck flask, fitted with a mechanical stirrer, condenser, thermometer, addition funnel and electric heating mantle, was placed 375 g (1.5 moles) methylenebis(4-phenyleneisocyanate) and 481 g methyl ethyl ketone (MEK). To this stirred heated solution (80°–83° C.) was added 554 g (1.0 mole) N-ethyl(perfluorooctane)sulfonamidoethyl alcohol over a 3 hour period and stirring and heating continued for an additional 3 hours.

To this stirred solution, containing fluorochemical urethane isocyanate and unreacted diisocyanate, was added 7.4 g camphene phenyl phosphine oxide, $C_{10}H_{16}POC_6H_5$, a carbodiimide-forming catalyst, and the reaction mixture was stirred and heated at about 80° C. for about 8 hours, at which time essentially all of the isocyanate groups had been converted to carbodiimide groups as indicated by IR absorption analysis.

The resulting solution of fluorochemical carbodiimide was then allowed to cool to room temperature and added over a one hour period to a stirred solution of 129 g (1.0 mole) dibutylamine in 129 g MEK maintained at 30° C. The resulting reaction mixture was heated for one hour at 50° C. to complete the conversion of essentially all carbodiimide groups to guanidine groups as indicated by IR analysis. The solid fluorochemical guanidine product (represented by structure 1 in Table 1), isolated in quantitative yield by evaporation of the MEK solvent under reduced pressure, was found to have a melting range of 75°–83° C.

EXAMPLES 2–14

Following the general procedure of Example 1, except employing the reagents in Table 2 and molar concentrations indicated in Table 3, the other fluorochemical guanidines of Table 1 were prepared. The reagents in Table 2 are identified by symbols, e.g. A-1, etc., for later reference.

TABLE 2

| | Alcohol Reagents |
|---|---|
| A-1 | $C_8F_{17}SO_2N(C_2H_5)C_2H_4OH$ |
| A-2 | $C_8F_{17}SO_2N(C_4H_9)C_2H_4OH$ |
| A-3 | $C_8F_{17}C_2H_4OH$ |
| A-4 | $(CH_3)_2CHCH_2OH$ |

Isocyanates

MDI 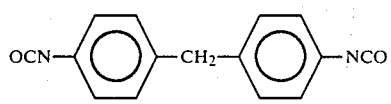

TABLE 2-continued

TDI: $OCN$—⟨⟩($CH_3$)—$NCO$

| | Imino Reagents |
|---|---|
| I-1 | $(C_4H_9)_2NH$ |
| I-2 | $(iso-C_3H_7)_2NH$ |
| I-3 | $(C_2H_5)_2NH$ |
| I-4 | $(CH_3)_2CHNH_2$ |
| I-5 | $C_{12}H_{25}NH_2$ |
| I-6 | O⟨⟩NH (morpholine) |
| I-7 | $(CH_3)_2NNH_2$ |
| I-8 | $(CH_3O)_3SiC_3H_6NH_2$ |
| I-9 | $C_8F_{17}SO_2N$⟨⟩$NH$ |
| I-10 | $C_8F_{17}SO_3$—⟨⟩—$NH_2$ |

TABLE 3

| Ex. No | Compound used* | Reactants (moles)** | | |
|---|---|---|---|---|
| | | Alcohol Reagent | Isocyanate | Imino Reagant |
| 2 | 2 | A-1 | MDI | I-2 |
| 3 | 3 | A-1 | MDI | I-3 |
| 4 | 4 | A-1 (2) | TDI (2.8) | I-4 (1.8) |
| 5 | 5 | A-1 | TDI | I-5 |
| 6 | 6 | A-1 | MDI | I-6 |
| 7 | 7 | A-1 | MDI | I-7 |
| 8 | 8 | A-1 | TDI | I-8 |
| 9 | 9 | A-1 | MDI | I-9 |
| 10 | 10 | A-4 | MDI | I-9 |
| 11 | 11 | A-1 | MDI | I-10 |
| 12 | 12 | A-2 | MDI | I-1 |
| 13 | 13 | A-3 | MDI | I-1 |
| 14 | 14 | A-3 | TDI | I-1 |

*The numbers correspond to the formula numbers of Table 1.
**All alcohol/isocyanate/imino reagent molar ratios were 2/3/2, except as indicated for Example 4.

In the following examples, the above-described fluorochemical guanidines of this invention were used to treat various textile substrates, and the treated articles evaluated for effectiveness of the fluorochemical treatment.

EXAMPLES 15-28

In these examples, undyed, level loop, nylon 6 carpet was treated in a padding operation (90% wet pickup) with an acetone solution of the fluorochemical guanidine (the concentration of which was in the range of 0.2 to 0.5% solids in order to deposit an amount of fluorochemical equivalent to 700 ppm. fluorine based on the weight of fiber), and 1.7% of a coconut oil based spin finish. The treated carpet was dried for 10 minutes at 50° C. and then heat set at 150° C. for 5 min., acid dyed, rinsed, dried (70° C., 30 min.), and cured (heated 130° C., 10 min.).

The oil repellency (OR), water repellency (WR) and walk-on soil resistance (WOS) were determined on the treated samples.

The water repellency test is one which is often used for this purpose. The aqueous stain or water repellency of treated samples is measured using a water/isopropyl alcohol test, and is expressed in terms of a water repellency rating of the treated carpet or fabric. Treated carpets which are penetrated by or resistant only to a 100 percent water/0 percent isopropyl alcohol mixture (the least penetrating of the test mixtures) are given a rating of 100/0, whereas treated fabrics resistant to a 0 percent water/100 percent isopropyl alcohol mixture (the most penetrating of the test mixtures) are given a rating of 0/100. Other intermediate values are determined by use of other water/isopropyl alcohol mixtures, in which the percentage amounts of water and isopropyl alcohol are each multiples of 10. The water repellency rating corresponds to the most penetrating mixture which does not penetrate or wet the fabric after 10 seconds contact. In general a water repellency rating of 90/10 or better, e.g, 80/20, is desirable.

The oil repellency test is also one which is often used for this purpose. The oil repellency of treated carpet and textile samples is measured by AATCC Standard Test 118-1978, which test is based on the resistance of treated fabric to penetration by oils of varying surface tensions. Treated fabrics resistant only to "Nujol", a brand of mineral oil and the least penetrating of the test oils, are given a rating of 1, whereas treated fabrics resistant to heptane (the most penetrating of the test oils) are given a value of 8. Other intermediate values are determined by use of other pure oils or mixtures of oils. The rated oil repellency corresponds to the most penetrating oil (or mixture of oils) which does not penetrate or wet the fabric after 10 sec. contact (rather than the 30 sec. contact of the Standard Test). Higher numbers indicate better oil repellency. In general, an oil repellency of 2 or greater is desirable.

The soil resistance of treated and untreated (control) carpet was determined by exposure to pedestrian traffic in accordance with AATCC Test Method 122-1979, the exposure site being a heavily travelled industrial area for an exposure of about 15,000 "traffics". The samples are repositioned periodically to insure uniform exposure and are vacuumed every 24 hours during the test and before visual evaluation. The evaluation employed the following "Walt-On-Sorting" (WOS) rating system:

| WOS Rating | Description |
| --- | --- |
| 0 | equal to control |
| ±½ | slightly better (+) or worse (−) than control |
| ±1 | impressive difference compared to control |
| ±1½ | very impressive difference compared to control |
| ±2 | extremely impressive difference compared to control |

The retention of fluorochemical guanidine on the treated carpet through the dyeing operation was determined by fluorine analysis before and after dyeing.

Results are set forth in Table 4.

TABLE 4

| Ex. No. | Formula of fluoro-chemical* | Amount Fluorine on Carpet, Before Dyeing, ppm | Amount Fluorine on Carpet, After Dyeing, ppm | Fluorine Retention, Percent | OR | WR | WOS |
| --- | --- | --- | --- | --- | --- | --- | --- |
| 15 | 1 | 625 | 445 | 71 | 1 | 60/40 | +1½ |
| 16 | 2 | 710 | 415 | 58 | 3 | 40/60 | +2 |
| 17 | 3 | 620 | 440 | 71 | 3 | 50/50 | +½ |
| 18 | 4 | 575 | 575 | 100 | 2 | 70/30 | 0 |
| 19 | 5 | 640 | 350 | 55 | 2 | 70/30 | 0 |
| 20 | 6 | 630 | 555 | 82 | 2 | 60/40 | +1½ |
| 21 | 7 | 665 | 425 | 64 | 2 | 70/30 | +½ |
| 22 | 8 | 525 | 460 | 82 | 1 | 80/20 | 0 |
| 23 | 9 | 720 | 305 | 42 | 1 | 70/30 | 0 |
| 24 | 10 | 545 | 435 | 80 | 1 | 70/30 | 0 |
| 25 | 11 | 775 | 405 | 52 | 2 | 70/30 | +½ |
| 26 | 12 | 680 | 455 | 67 | 2 | 50/50 | +1 |
| 27 | 13 | 585 | 435 | 65 | 2 | 70/30 | +1 |
| 28 | 14 | 750 | 380 | 51 | 2 | 70/30 | 0 |
| C | None | 0 | 0 | 0 | 0 | NWR** | 0 |

*The numbers correspond to formulas of fluorochemical guanidines given in Table 1
**"NWR" means no water repellency.

The data of Table 4 show that oil and water repellency was obtained for all the fluorochemical guanidines used, and soil resistance was obtained for many of them. Particularly noteworthy were the relatively high retention values (after dyeing) which were obtained for most of the fluorochemical quanidines.

EXAMPLES 29-32

Two different rainwear fabrics were treated with a 25% aqueous emulsion of the fluorochemical guanidines of formula 6 of Table 1 (using "Tween 80" polyoxyethylene sorbitan monoleate and $C_8F_{17}SO_2NHC_3H_6N(CH_3)_3Cl$ emulsifiers) in a padding operation, dried at 150° C. for 10 minutes, and evaluated for initial OR and resistance to a water spray (SR), then these properties evaluated again after 5 launderings (5L) and dry cleaning (DC). The OR test used was the above-described AATCC Standard Test 118-1978, the contact time before observation being the specified 30 sec., an OR value of 3 or greater being particularly desirable.

The water spray rating (SR) is measured by AATCC Test Method 22-1979. The spray rating is measured using a 0 to 100 scale where 100 is the highest possible rating. In general, a spray rating of 70 or greater is desirable, particularly for outerwear fabrics.

The treated fabrics were laundered using a mechanically agitated automatic washing machine capable of containing a 4 Kg. load, using water at 50° C. and a commercial detergent, and then the washed fabrics were tumble-dried in an automatic dryer for 40 minutes at 70° C. and pressed in a flat-bed press (at 154° C.) before testing.

The treated fabrics were dry cleaned using perchloroethylene containing 1% of a dry cleaning detergent and tumbling in a motor driven tumble jar (AATCC Test Method 70-1975) for 20 minutes at 25° C. After removing excess solvent in a wringer, samples were dried at 70° C. for 10 minutes, then pressed on each side for 15 seconds on a flat-bed press maintained at 154° C.

The runs are summarized in Table 5 together with runs using blends of the fluorochemical guanidine with a commercial fluorochemical used to impart oil and water repellency. Table 5 also includes comparative runs, C-1, C-2, where no fluorochemical was used in the padding operation.

TABLE 5

| Ex. No. | Fluoro-chemical Used | Fab-ric$^a$ | % SOF$^b$ | Initial OR | Initial SR | 5L OR | 5L SR | DC OR | DC SR |
|---|---|---|---|---|---|---|---|---|---|
| 29 | No. 6 of Table 1 | A | 0.2 | 4.5 | 60 | 3.5 | 70 | 1.5 | 50 |
| 30 | No. 6 of Table 1 | B | 0.2 | 5 | 75 | 3 | 70 | 1.5 | 70 |
| 31 | blend$^c$ | A | 0.2 | 6.5 | 100 | 5.5 | 75 | 6 | 85 |
| 32 | blend$^c$ | B | 0.2 | 6.5 | 100 | 4 | 80 | 6.5 | 100 |
| C-1 | — | A | 0 | 0 | 0 | 0 | 0 | 0 | 0 |
| C-2 | — | B | 0 | 0 | 0 | 0 | 0 | 0 | 0 |

$^a$Fabric A was 100% nylon taffeta. Fabric B was 100% woven polyester.
$^b$% SOF means % fluorochemical solids on fabric.
$^c$The blend was a mixture of 65 parts of a commercial fluorochemical acrylate copolymer used to treat rainwear and 35 parts of fluorochemical guanidine of formula 6.

The data of Table 5 show useful initial oil and water repellency was obtained for the rainwear fabric when the fluorochemical used was just the fluorochemical guanidine, although laundering and dry cleaning decreased the oil repellency. However, as shown by runs 31, 32, when the blend was used, the repellency did not decrease as much after laundering and dry cleaning.

EXAMPLE 33

A sample of nylon carpet (50 oz/yd$^2$) was top sprayed with an aqueous emulsion of fluorochemical guanidine (25% aqueous pickup) to impart 0.1% SOF. The treated carpet was dried at 70° C. and then cured (heated) at 130° C. for 10 min. and found to have OR of 1, WR of 80/20 and, most noteworthy, a WOS of +1½ to +2.

EXAMPLE 34

The fluorochemical guanidine number 6 of Table 1 was applied as an aqueous dispersion bath at various concentrations to water-leaf paper sheets using a laboratory size press (yielding 82% wet pickup) and the sheets dried in a photo sheet dryer at 150° C. and evaluated for oil and water repellency. The results are given in Table 6.

TABLE 6

| Run | Concentration of fluorochemical guanidine in bath, wt. % | Amount of fluorochemical on paper, wt. % | Oil repellency$^a$ | Water repellency$^b$ |
|---|---|---|---|---|
| 1 | 0.37 | 0.3 | 5 | 64 |
| 2 | 0.61 | 0.5 | 6 | 22 |
| 3 | 1.22 | 1.0 | 8 | 24 |
| 4 | 0 | None | 0 | NWR |

$^a$This was determined by the "Kit Test" described as TAPPI Useful Method 557; the higher the value the better the repellency.
$^b$This was determined by the "Cobb Test" described as TAPPI-T441-OS-77; the lower the value, the better the water repellency.

The data in the above table show that the fluorochemical guanidine of this invention imparted useful oil repellency, albeit a relatively large amount of the fluorochemical was required. The fluorochemical guanidine may be used in conjunction with hydrocarbon treating agents for paper, e.g. ketene dimers, commonly used to impart the desired water repellency.

EXAMPLE 35

This example describes the treatment of a carpet fiber with a fluorochemical guanidine of this invention in combination with a spin finish lubricant and the testing of the dyed carpet prepared from the treated fibers.

A neat oil spin finish consisting of 13.1% of the fluorochemical guanidine with formula number 1 of Table 1, 46.2% of a coconut oil-based fiber lubricant, and 40.7% butoxyethoxyethanol was applied to freshly melt-extruded, undrawn yarn of nylon 6 carpet denier fibers. The fluorochemical guanidine was applied with a commercial spin finish applicator. The thus treated yarn was continuously drawn and texturized, plied to form a two-ply yarn, heat set at 190° C. for one minute, and then made into cut pile carpet. The carpet was acid dyed by three different processes, dried, and then evaluated for oil and water repellency, walk-on soiling resistance, and retention of fluorochemical treatment through the dyeing processes. Control runs were also conducted in the same manner, except that the fluorochemical treatment was omitted; the OR, WR, and WOS values obtained for the control runs were all zero. The testing results are in Table 7.

TABLE 7

| Run | Amount Fluroine on Carpet Before Dyeing, ppm | Amount Fluroine on Carpet After Dyeing, ppm | Fluorine Retention, Percent | OR | WR | WOS |
|---|---|---|---|---|---|---|
| 1 | 430 | 420$^a$ | 98 | 2 | 70/30 | 0 |
| 2 | 430 | 400$^b$ | 93 | 2.5 | 40/60 | +1 |
| 3 | 430 | 350$^c$ | 81 | 2.5 | 40/60 | 0 |

$^a$Continuous dye process
$^b$Beck dye process (batch)
$^c$Continuous pad dye process.

The data of Table 7 show that outstanding fluorine retention through dyeing and good oil and water repellency were obtained, and better soil resistance was obtained for Beck dyed fiber controls.

Various modifications and alterations of this invention will become apparent to those skilled in the art without departing from the scope and spirit of this invention.

What is claimed is:

1. Normally solid, water-insoluble, fluorochemical guanidine compositions which are fluoroaliphatic radical-containing, substituted guanidine compounds, or compositions comprising mixtures thereof, said compounds having one or more monovalent fluoroaliphatic radicals having at least three fully fluorinated carbon atoms and one or more substituted guanidino moieties of the formula

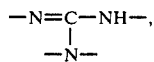

said radicals and moieties being bonded together by linking groups selected from aliphatic, aromatic, oxy, thio, carbonyl, sulfone, sulfoxy, —N(CH₃)—, sulfonamido, carbonamido, sulonamidoalkylene, carbonamidolkylene, carbonyloxy, urethane, urea, and combinations thereof, with the proviso that when only one guanidino moiety is present, and only two organic substituents are in said guanidino moiety, said substituents must be on different nitrogen atoms of the moiety, and when more than one guanidine moiety is present, said moieties are bonded together by divalent linking groups selected from the group consisting of alkylene, aralkylene, arylene, polyoxyalkylene, and combinations thereof and can contain said fluoroaliphatic radical.

2. A fluorochemical guanidine represented by the formula

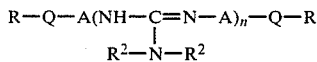

where R—Q is $C_8F_{17}SO_2N(C_2H_5)C_2H_4OCONH—$, A is —$C_6H_4CH_2C_6H_4$—,

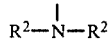

is —$N(C_4H_9)_2$, and n is 2.

3. A fluorochemical guanidine represented by the formula

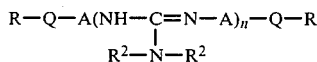

where R—Q is $C_8F_{17}SO_2N(C_2H_5)C_2H_4OCONH—$, A is —$C_6H_4CH_2C_6H_4$—, $R^2$—N—$R^2$ is

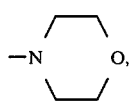

and n is 1 to 6.

4. A fluorochemical guanidine represented by the formula

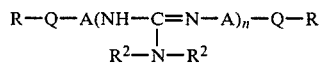

where R—Q is $C_8F_{17}SO_2N(C_2H_5)C_2H_4OCONH—$, A is —$C_6H_4CH_2C_6H_4$—, $R^2$—N—$R^2$ is —$N(iso—C_3H_7)_2$, and n is 1 to 6.

5. A fiber comprising an organic solution or aqueous dispersion comprising the fluorochemical guanidine composition of claim 1.

6. The fiber finish according to claim 5 further comprising a fiber lubricant.

7. A method for imparting oil and water repellency to a fibrous substrate, which comprises treating the surface thereof with the fiber finish of claim 5.

8. In the manufacture of spun synthetic organic fibers wherein a fiber finish is applied to said fibers, the improvement comprising employing as said fiber finish the fiber finish of claim 6.

9. A fibrous substrate coated with the fluorochemical guanidine composition of claim 1.

10. A fibrous substrate according to claim 9 wherein said substrate is nylon carpet fiber.

11. A fluorochemical guanidine represented by the formula

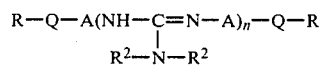

where R—Q is $C_8F_{17}SO_2N(C_2H_5)C_2H_4OCONH—$, A is —$CH_2C_6H_4CH_2$—, $R^2$—N—$R^2$ is —$N(C_4H_9)_2$, and n is 1 to 6.

12. A fluorochemical guanidine represented by the formula

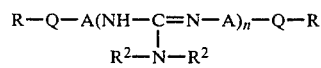

where R—Q is $C_8F_{17}SO_2N(C_2H_5)C_2H_4OCONH—$, A is —$CH_2C_6H_4CH_2$—, $R^2$—N—$R^2$ is

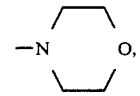

and n is 1 to 6.

13. A fluorochemical guanidine represented by the formula

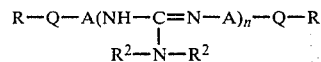

where R—Q is $C_8F_{17}SO_2N(C_2H_5)C_2H_4OCONH—$, A is —$CH_2C_6H_4CH_2$—, $R^2$—N—$R^2$ is —$N(iso—C_3H_7)_2$, and n is 1 to 6.

14. Normally solid, water-insoluble, fluorochemical guanidine compositions which are fluoroaliphatic radical-containing substituted guanidine compounds or compositions comprising a mixture of such compounds, said compounds being represented by the general formula

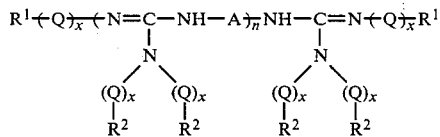

where n is 0 to 20, x is 0 to 1, $R^1$ and $R^2$ are hydrogen atoms, a monovalent fluoroaliphatic radical, $R_f$, having at least three fully fluorinated carbon atoms, or an organic radical selected from the group consisting of alkyl, cycloalkyl, aryl, and combinations thereof, A is a divalent linking group selected from the group consisting of alkylene, aralkylene, arylene polyoxyalkylene, and combinations thereof, which can contain said $R_f$, and Q is a divalent hetero atom-containing or organic linking group selected from the group consisting of aliphatic aromatic aralkyl, fluoroaliphatic, and combinations thereof, with the proviso that at least one fluoroaliphatic radical, $R_f$, is present in one or more of the $R^1$, $R^2$, and A groups, that where $R^1$ or $R^2$ is $R_f$, x is 1, and that when only one guanidino moiety is present and only two organic substituents are in said guanidino moiety, said substituents must be on different nitrogen atoms.

15. Fluorochemical guanidine compositions according to claim 14 wherein said $R^1$ and $R^2$ have no more than about 18 carbon atoms.

16. Fluorochemical guanidine compositions according to claim 14 wherein two $R^2$ groups of a guanidino are bonded together to form a cyclic structure with the adjacent nitrogen atom of that guanidino group.

17. Fluorochemical guanidine compositions according to claim 14 wherein said $R^1$, $R^2$, A, and Q are free of active hydrogen atoms that can react readily with isocyanate under urethane bond forming conditions.

* * * * *

UNITED STATES PATENT AND TRADEMARK OFFICE
CERTIFICATE OF CORRECTION

PATENT NO. : 4,540,497

DATED : September 10, 1985

INVENTOR(S) : John C. Chang; Richard D. Howells

It is certified that error appears in the above-identified patent and that said Letters Patent is hereby corrected as shown below:

Col. 14, line 13, "Walt-On-Sorting" should be --Walk-On-Soiling--.

Col. 17, line 17, "Sulonamidoalkylene" should be --sulfonamidoalkylene--.

Col. 17, line 18, "bonamidolkylene" should be --bonamidoalkylene--.

Col. 17, line 23, "guanidine" should be --guanidino--.

Col. 18, line 1, after the word "fiber" insert --finish--.

Signed and Sealed this

Fourteenth Day of January 1986

[SEAL]

Attest:

DONALD J. QUIGG

Attesting Officer

Commissioner of Patents and Trademarks